(12) United States Patent
Zingalis et al.

(10) Patent No.: US 12,185,995 B2
(45) Date of Patent: Jan. 7, 2025

(54) BONE STABILIZATION SYSTEMS

(71) Applicant: GLOBUS MEDICAL, INC., Audubon, PA (US)

(72) Inventors: Gabrielle Zingalis, Philadelphia, PA (US); Peter Govey, Ardmore, PA (US); Peter Evans, Lafayette Hill, PA (US)

(73) Assignee: Globus Medical, Inc., Audubon, PA (US)

( * ) Notice: Subject to any disclaimer, the term of this patent is extended or adjusted under 35 U.S.C. 154(b) by 658 days.

(21) Appl. No.: 16/597,381

(22) Filed: Oct. 9, 2019

(65) Prior Publication Data

US 2021/0106368 A1   Apr. 15, 2021

(51) Int. Cl.
*A61B 17/80* (2006.01)

(52) U.S. Cl.
CPC ...... *A61B 17/8061* (2013.01); *A61B 17/8057* (2013.01)

(58) Field of Classification Search
CPC .............. A61B 17/8061; A61B 17/8057
See application file for complete search history.

(56) References Cited

U.S. PATENT DOCUMENTS

| | | |
|---|---|---|
| 1,105,105 A | 7/1914 | Sherman |
| 2,486,303 A | 10/1949 | Longfellow |
| 3,463,148 A | 8/1969 | Treace |
| 3,695,259 A | 10/1972 | Yost |
| 3,716,050 A | 2/1973 | Johnston |
| 4,219,015 A | 8/1980 | Steinemann |
| 4,493,317 A | 1/1985 | Klaue |
| 4,524,765 A | 6/1985 | de Zbikowski |
| 4,651,724 A | 3/1987 | Berentey et al. |
| 4,683,878 A | 8/1987 | Carter |
| 4,781,183 A | 11/1988 | Casey et al. |
| 4,867,144 A | 9/1989 | Karas et al. |
| 4,923,471 A | 5/1990 | Morgan |
| 4,966,599 A | 10/1990 | Pollock |
| 5,002,544 A | 3/1991 | Klaue et al. |
| 5,041,114 A | 8/1991 | Chapman et al. |
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Luhr et al. |
| 5,423,826 A | 6/1995 | Coates et al. |
| 5,468,242 A | 11/1995 | Reisberg |
| D365,634 S | 12/1995 | Morgan |
| 5,489,305 A | 2/1996 | Morgan |
| 5,527,311 A | 6/1996 | Procter et al. |
| 5,578,036 A | 11/1996 | Stone et al. |

(Continued)

FOREIGN PATENT DOCUMENTS

| | | |
|---|---|---|
| CN | 201987653 U | 9/2011 |
| CN | 202313691 U | 7/2012 |

(Continued)

*Primary Examiner* — Jerrah Edwards
*Assistant Examiner* — Christine L Nelson

(57) ABSTRACT

Bone plates for engaging bone members are described herein. The bone plates can include features that accommodate the underlying anatomy of different types of bone, such as the proximal portion of the ulna. The bone plate can receive one or more fasteners to secure the bone plate to the proximal ulna. A reverse angle fastener may be included to target the olecranon process of the proximal ulna.

19 Claims, 8 Drawing Sheets

(56) References Cited

U.S. PATENT DOCUMENTS

| | | |
|---|---|---|
| 5,601,553 A | 2/1997 | Trebing et al. |
| 5,676,667 A | 10/1997 | Hausman |
| 5,690,631 A | 11/1997 | Duncan et al. |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,746,742 A | 5/1998 | Runciman et al. |
| 5,766,175 A | 6/1998 | Martinotti |
| 5,766,176 A | 6/1998 | Duncan |
| 5,779,706 A | 7/1998 | Tschakaloff |
| 5,785,712 A | 7/1998 | Runciman et al. |
| 5,797,914 A | 8/1998 | Leibinger |
| 5,814,048 A | 9/1998 | Morgan |
| 5,925,048 A | 7/1999 | Ahmad et al. |
| 5,938,664 A | 8/1999 | Winquist et al. |
| 5,961,519 A | 10/1999 | Bruce et al. |
| 5,980,540 A | 11/1999 | Bruce |
| 6,001,099 A | 12/1999 | Huebner |
| 6,071,291 A | 6/2000 | Forst et al. |
| 6,093,201 A | 7/2000 | Cooper et al. |
| 6,096,040 A | 8/2000 | Esser |
| 6,107,718 A | 8/2000 | Schustek et al. |
| 6,152,927 A | 11/2000 | Farris et al. |
| 6,206,881 B1 | 3/2001 | Frigg et al. |
| 6,283,969 B1 | 9/2001 | Grusin et al. |
| 6,309,393 B1 | 10/2001 | Tepic et al. |
| 6,322,562 B1 | 11/2001 | Wolter |
| 6,364,882 B1 | 4/2002 | Orbay |
| D458,683 S | 6/2002 | Bryant et al. |
| D458,684 S | 6/2002 | Bryant et al. |
| 6,533,786 B1 | 3/2003 | Needham et al. |
| D479,331 S | 9/2003 | Pike et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,866,665 B2 | 3/2005 | Orbay |
| 6,955,677 B2 | 10/2005 | Dahners |
| 6,974,461 B1 | 12/2005 | Wolter |
| 7,001,387 B2 | 2/2006 | Farris et al. |
| 7,063,701 B2 | 6/2006 | Michelson |
| 7,090,676 B2 | 8/2006 | Huebner et al. |
| 7,128,744 B2 | 10/2006 | Weaver et al. |
| 7,137,987 B2 | 11/2006 | Patterson et al. |
| 7,153,309 B2 | 12/2006 | Huebner et al. |
| 7,179,260 B2 | 2/2007 | Gerlach et al. |
| 7,250,053 B2 | 7/2007 | Orbay |
| 7,294,130 B2 | 11/2007 | Orbay |
| 7,322,983 B2 | 1/2008 | Harris |
| 7,341,589 B2 | 3/2008 | Weaver et al. |
| 7,344,538 B2 | 3/2008 | Myerson et al. |
| 7,354,441 B2 | 4/2008 | Frigg |
| 7,604,657 B2 | 10/2009 | Orbay et al. |
| 7,632,277 B2 | 12/2009 | Woll et al. |
| 7,635,381 B2 | 12/2009 | Orbay |
| 7,637,928 B2 | 12/2009 | Fernandez |
| 7,655,029 B2 | 2/2010 | Niederberger et al. |
| 7,655,047 B2 | 2/2010 | Swords |
| 7,695,472 B2 | 4/2010 | Young |
| 7,717,946 B2 | 5/2010 | Oepen et al. |
| 7,722,653 B2 | 5/2010 | Young et al. |
| 7,740,648 B2 | 6/2010 | Young et al. |
| D622,853 S | 8/2010 | Raven, III |
| 7,771,457 B2 | 8/2010 | Kay et al. |
| 7,776,076 B2 | 8/2010 | Grady, Jr. et al. |
| 7,857,838 B2 | 12/2010 | Orbay |
| 7,867,260 B2 | 1/2011 | Meyer et al. |
| 7,867,261 B2 | 1/2011 | Sixto, Jr. et al. |
| 7,875,062 B2 | 1/2011 | Lindemann et al. |
| 7,905,910 B2 | 3/2011 | Gerlach et al. |
| 7,909,858 B2 | 3/2011 | Gerlach et al. |
| 7,951,178 B2 | 5/2011 | Jensen |
| 7,951,179 B2 | 5/2011 | Matityahu |
| 7,976,570 B2 | 7/2011 | Wagner et al. |
| D643,121 S | 8/2011 | Millford et al. |
| D646,785 S | 10/2011 | Milford |
| 8,043,297 B2 | 10/2011 | Grady, Jr. et al. |
| 8,057,520 B2 | 11/2011 | Ducharme et al. |
| 8,062,296 B2 | 11/2011 | Orbay et al. |
| 8,100,953 B2 | 1/2012 | White et al. |
| 8,105,367 B2 | 1/2012 | Austin et al. |
| 8,114,081 B2 | 2/2012 | Kohut et al. |
| 8,118,846 B2 | 2/2012 | Leither et al. |
| 8,118,848 B2 | 2/2012 | Ducharme et al. |
| 8,162,950 B2 | 4/2012 | Digeser et al. |
| 8,167,918 B2 | 5/2012 | Strnad et al. |
| 8,177,820 B2 | 5/2012 | Anapliotis et al. |
| 8,246,661 B2 | 8/2012 | Beutter et al. |
| 8,252,032 B2 | 8/2012 | White et al. |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,317,842 B2 | 11/2012 | Graham et al. |
| 8,323,321 B2 | 12/2012 | Gradl |
| 8,337,535 B2 | 12/2012 | White et al. |
| 8,343,155 B2 | 1/2013 | Fisher et al. |
| 8,382,807 B2 | 2/2013 | Austin et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 | 3/2013 | Ralph et al. |
| 8,419,775 B2 | 4/2013 | Orbay et al. |
| 8,435,272 B2 | 5/2013 | Dougherty et al. |
| 8,439,918 B2 | 5/2013 | Gelfand |
| 8,444,679 B2 | 5/2013 | Ralph et al. |
| 8,491,593 B2 | 7/2013 | Prien et al. |
| 8,506,608 B2 | 8/2013 | Cerynik et al. |
| 8,512,384 B2 | 8/2013 | Beutter et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,540,755 B2 | 9/2013 | Whitmore |
| 8,551,095 B2 | 10/2013 | Fritzinger et al. |
| 8,551,143 B2 | 10/2013 | Norris et al. |
| 8,568,462 B2 | 10/2013 | Sixto, Jr. et al. |
| 8,574,268 B2 | 11/2013 | Chan et al. |
| 8,597,334 B2 | 12/2013 | Mocanu |
| 8,603,147 B2 | 12/2013 | Sixto, Jr. et al. |
| 8,617,224 B2 | 12/2013 | Kozak et al. |
| 8,632,574 B2 | 1/2014 | Kortenbach et al. |
| 8,641,741 B2 | 2/2014 | Murashko, Jr. |
| 8,641,744 B2 | 2/2014 | Weaver et al. |
| 8,663,224 B2 | 3/2014 | Overes et al. |
| 8,728,082 B2 | 5/2014 | Fritzinger et al. |
| 8,728,126 B2 | 5/2014 | Steffen |
| 8,740,905 B2 | 6/2014 | Price et al. |
| 8,747,442 B2 | 6/2014 | Orbay et al. |
| 8,764,751 B2 | 7/2014 | Orbay et al. |
| 8,764,808 B2 | 7/2014 | Gonzalez-Hernandez |
| 8,777,998 B2 | 7/2014 | Daniels et al. |
| 8,790,376 B2 | 7/2014 | Fritzinger et al. |
| 8,790,377 B2 | 7/2014 | Ralph et al. |
| 8,808,333 B2 | 8/2014 | Kuster et al. |
| 8,808,334 B2 | 8/2014 | Strnad et al. |
| 8,834,532 B2 | 9/2014 | Velikov et al. |
| 8,834,537 B2 | 9/2014 | Castanada et al. |
| 8,852,246 B2 | 10/2014 | Hansson |
| 8,852,249 B2 | 10/2014 | Ahrens et al. |
| 8,864,802 B2 | 10/2014 | Schwager et al. |
| 8,870,931 B2 | 10/2014 | Dahners et al. |
| 8,888,825 B2 | 11/2014 | Batsch et al. |
| 8,906,076 B2 | 12/2014 | Mocanu et al. |
| 8,911,482 B2 | 12/2014 | Lee et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |

(56) References Cited

U.S. PATENT DOCUMENTS

| | | | |
|---|---|---|---|
| 8,951,291 B2 | 2/2015 | Impellizzeri | |
| 8,968,368 B2 | 3/2015 | Tepic | |
| 9,011,457 B2 | 4/2015 | Grady, Jr. et al. | |
| 9,023,052 B2 | 5/2015 | Lietz et al. | |
| 9,050,151 B2 | 6/2015 | Schilter | |
| 9,072,555 B2 | 7/2015 | Michel | |
| 9,072,557 B2 | 7/2015 | Fierlbeck et al. | |
| 9,107,678 B2 | 8/2015 | Murner et al. | |
| 9,107,711 B2 | 8/2015 | Hainard | |
| 9,107,713 B2 | 8/2015 | Horan et al. | |
| 9,107,718 B2 | 8/2015 | Isch | |
| 9,113,970 B2 | 8/2015 | Lewis et al. | |
| 9,149,310 B2 | 10/2015 | Fritzinger et al. | |
| 9,161,791 B2 | 10/2015 | Frigg | |
| 9,161,795 B2 | 10/2015 | Chasbrummel et al. | |
| 9,168,075 B2 | 10/2015 | Dell'Oca | |
| 9,179,950 B2 | 11/2015 | Zajac et al. | |
| 9,179,956 B2 | 11/2015 | Cerynik et al. | |
| 9,180,020 B2 | 11/2015 | Gause et al. | |
| 9,211,151 B2 | 12/2015 | Weaver et al. | |
| 9,259,217 B2 | 2/2016 | Fritzinger et al. | |
| 9,259,255 B2 | 2/2016 | Lewis et al. | |
| 9,271,769 B2 | 3/2016 | Batsch et al. | |
| 9,283,010 B2 | 3/2016 | Medoff et al. | |
| 9,295,506 B2 | 3/2016 | Raven, III et al. | |
| 9,314,284 B2 | 4/2016 | Chan et al. | |
| 9,320,554 B2 | 4/2016 | Greenberg et al. | |
| 9,322,562 B2 | 4/2016 | Takayama et al. | |
| 9,370,388 B2 | 6/2016 | Globerman et al. | |
| D765,851 S | 9/2016 | Early et al. | |
| 9,433,407 B2 | 9/2016 | Fritzinger et al. | |
| 9,433,452 B2 | 9/2016 | Weiner et al. | |
| 9,468,479 B2 | 10/2016 | Marotta et al. | |
| 9,480,512 B2 | 11/2016 | Orbay | |
| 9,486,262 B2 | 11/2016 | Andermahr et al. | |
| 9,492,213 B2 | 11/2016 | Orbay | |
| 9,510,878 B2 | 12/2016 | Nanavati et al. | |
| 9,510,880 B2 | 12/2016 | Terrill et al. | |
| 9,526,543 B2 | 12/2016 | Castaneda et al. | |
| 9,545,277 B2 | 1/2017 | Wolf et al. | |
| 9,549,819 B1 | 1/2017 | Bravo et al. | |
| 9,566,097 B2 | 2/2017 | Fierlbeck et al. | |
| 9,579,133 B2 | 2/2017 | Guthlein | |
| 9,622,799 B2 | 4/2017 | Orbay et al. | |
| 9,636,157 B2 | 5/2017 | Medoff | |
| 9,649,141 B2 | 5/2017 | Raven, III et al. | |
| 9,668,794 B2 | 6/2017 | Kuster et al. | |
| 9,801,670 B2 | 10/2017 | Hashmi et al. | |
| 9,814,504 B2 | 11/2017 | Ducharme et al. | |
| 11,197,682 B2 * | 12/2021 | Langdale | A61B 17/8057 |
| 2002/0045901 A1 | 4/2002 | Wagner et al. | |
| 2004/0097937 A1 | 5/2004 | Pike et al. | |
| 2004/0116930 A1 | 6/2004 | O'Driscoll et al. | |
| 2005/0107796 A1 | 5/2005 | Gerlach et al. | |
| 2005/0131413 A1 | 6/2005 | O'Driscoll et al. | |
| 2005/0187551 A1 | 8/2005 | Orbay et al. | |
| 2006/0149265 A1 | 7/2006 | James et al. | |
| 2006/0241607 A1 | 10/2006 | Myerson et al. | |
| 2007/0173840 A1 | 7/2007 | Huebner | |
| 2007/0270849 A1 | 11/2007 | Orbay et al. | |
| 2007/0288022 A1 | 12/2007 | Lutz | |
| 2008/0021477 A1 | 1/2008 | Strnad et al. | |
| 2008/0234749 A1 | 9/2008 | Forstein | |
| 2008/0275510 A1 | 11/2008 | Schonhardt et al. | |
| 2009/0024172 A1 | 1/2009 | Pizzicara | |
| 2009/0024173 A1 | 1/2009 | Reis, Jr. | |
| 2009/0118773 A1 | 5/2009 | James et al. | |
| 2009/0198285 A1 | 8/2009 | Raven, III | |
| 2009/0228010 A1 | 9/2009 | Gonzalez-Hernandez et al. | |
| 2009/0228047 A1 | 9/2009 | Derouet et al. | |
| 2009/0248084 A1 | 10/2009 | Hintermann | |
| 2009/0281543 A1 | 11/2009 | Orbay et al. | |
| 2009/0299369 A1 | 12/2009 | Orbay et al. | |
| 2009/0312760 A1 | 12/2009 | Forstein et al. | |
| 2010/0057086 A1 | 3/2010 | Price et al. | |
| 2010/0114097 A1 | 5/2010 | Siravo et al. | |
| 2010/0121326 A1 | 5/2010 | Woll et al. | |
| 2010/0274247 A1 | 10/2010 | Grady, Jr. et al. | |
| 2011/0106086 A1 | 5/2011 | Laird | |
| 2011/0218580 A1 | 9/2011 | Schwager et al. | |
| 2012/0010667 A1 | 1/2012 | Eglseder | |
| 2012/0059424 A1 | 3/2012 | Epperly et al. | |
| 2012/0203227 A1 | 8/2012 | Martin | |
| 2012/0232599 A1 | 9/2012 | Schoenly et al. | |
| 2012/0323284 A1 | 12/2012 | Baker et al. | |
| 2013/0018426 A1 | 1/2013 | Tsai et al. | |
| 2013/0046347 A1 | 2/2013 | Cheng et al. | |
| 2013/0060291 A1 | 3/2013 | Petersheim | |
| 2013/0123841 A1 | 5/2013 | Lyon | |
| 2013/0138156 A1 | 5/2013 | Derouet | |
| 2013/0150902 A1 | 6/2013 | Leite | |
| 2013/0165981 A1 | 6/2013 | Clasbrummet et al. | |
| 2013/0211463 A1 | 8/2013 | Mizuno et al. | |
| 2013/0289630 A1 | 10/2013 | Fritzinger | |
| 2014/0005728 A1 | 1/2014 | Koay et al. | |
| 2014/0018862 A1 | 1/2014 | Koay et al. | |
| 2014/0031879 A1 | 1/2014 | Sixto, Jr. et al. | |
| 2014/0066998 A1 | 3/2014 | Martin | |
| 2014/0094856 A1 | 4/2014 | Sinha | |
| 2014/0121710 A1 | 5/2014 | Weaver et al. | |
| 2014/0148859 A1 | 5/2014 | Taylor et al. | |
| 2014/0180345 A1 | 6/2014 | Chan et al. | |
| 2014/0277178 A1 | 9/2014 | O'Kane et al. | |
| 2014/0277181 A1 | 9/2014 | Garlock | |
| 2014/0316473 A1 | 10/2014 | Pfeffer et al. | |
| 2014/0330320 A1 | 11/2014 | Wolter | |
| 2014/0378975 A1 | 12/2014 | Castaneda et al. | |
| 2015/0051650 A1 | 2/2015 | Verstreken et al. | |
| 2015/0051651 A1 | 2/2015 | Terrill et al. | |
| 2015/0073486 A1 | 3/2015 | Marotta et al. | |
| 2015/0105829 A1 | 4/2015 | Laird | |
| 2015/0112355 A1 | 4/2015 | Dahners et al. | |
| 2015/0134011 A1 | 5/2015 | Medoff | |
| 2015/0142065 A1 | 5/2015 | Schonhardt et al. | |
| 2015/0190185 A1 | 7/2015 | Koay et al. | |
| 2015/0209091 A1 | 7/2015 | Sixto, Jr. et al. | |
| 2015/0216571 A1 | 8/2015 | Impellizzeri | |
| 2015/0223852 A1 | 8/2015 | Lietz et al. | |
| 2015/0272638 A1 | 10/2015 | Langford | |
| 2015/0282851 A1 | 10/2015 | Michel | |
| 2015/0313653 A1 | 11/2015 | Ponce et al. | |
| 2015/0313654 A1 | 11/2015 | Horan et al. | |
| 2015/0327898 A1 | 11/2015 | Martin | |
| 2015/0351816 A1 | 12/2015 | Lewis et al. | |
| 2015/0374421 A1 | 12/2015 | Rocci et al. | |
| 2016/0022336 A1 | 1/2016 | Bateman | |
| 2016/0030035 A1 | 2/2016 | Zajac et al. | |
| 2016/0045237 A1 | 2/2016 | Cerynik et al. | |
| 2016/0045238 A1 | 2/2016 | Bohay et al. | |
| 2016/0074081 A1 | 3/2016 | Weaver et al. | |
| 2016/0166297 A1 | 6/2016 | Mighell et al. | |
| 2016/0166298 A1 * | 6/2016 | Mighell | A61B 17/0401 606/280 |
| 2016/0183990 A1 | 6/2016 | Koizumi et al. | |
| 2016/0228167 A1 * | 8/2016 | Wahl | A61B 17/8057 |
| 2016/0262814 A1 | 9/2016 | Wainscott | |
| 2016/0278828 A1 | 9/2016 | Ragghianti | |
| 2016/0310183 A1 | 10/2016 | Shah et al. | |
| 2016/0310185 A1 | 10/2016 | Sixto et al. | |
| 2016/0324552 A1 | 11/2016 | Baker et al. | |
| 2016/0354122 A1 | 12/2016 | Montello et al. | |
| 2017/0035478 A1 | 2/2017 | Andermahr et al. | |
| 2017/0042592 A1 | 2/2017 | Kim | |
| 2017/0042596 A9 | 2/2017 | Mighell et al. | |
| 2017/0049493 A1 | 2/2017 | Gauneau et al. | |
| 2017/0056081 A1 | 3/2017 | Langdale et al. | |
| 2017/0065312 A1 | 3/2017 | Lauf et al. | |
| 2017/0105775 A1 | 4/2017 | Ricker et al. | |
| 2017/0215931 A1 | 8/2017 | Cremer et al. | |

(56) References Cited

U.S. PATENT DOCUMENTS

| | | | |
|---|---|---|---|
| 2018/0049782 A1 | 2/2018 | Gahman et al. | |
| 2018/0256226 A1* | 9/2018 | Govey | A61B 17/72 |

FOREIGN PATENT DOCUMENTS

| | | |
|---|---|---|
| CN | 202821574 U | 3/2013 |
| CN | 202821575 U | 3/2013 |
| CN | 203506858 U | 4/2014 |
| CN | 203815563 U | 9/2014 |
| CN | 104083201 B | 1/2016 |
| CN | 105982727 A | 10/2016 |
| FR | 2846870 A1 | 5/2004 |
| FR | 2928259 A1 | 9/2009 |
| JP | 2003210478 A | 7/2003 |
| TW | 201316942 A | 5/2013 |
| WO | 2016079504 A1 | 5/2016 |

* cited by examiner

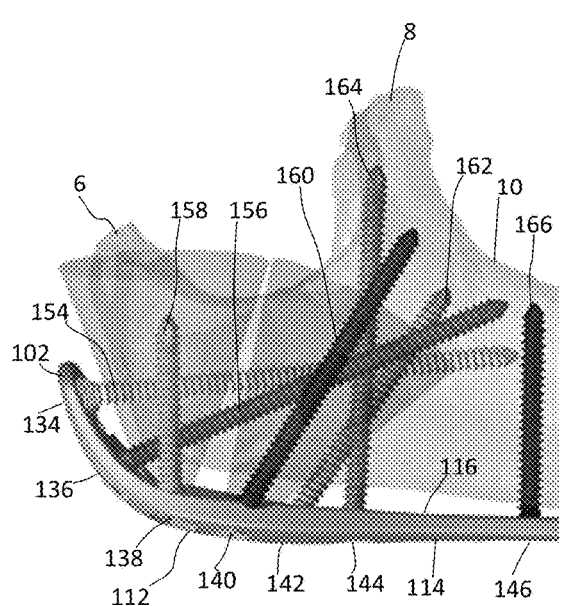
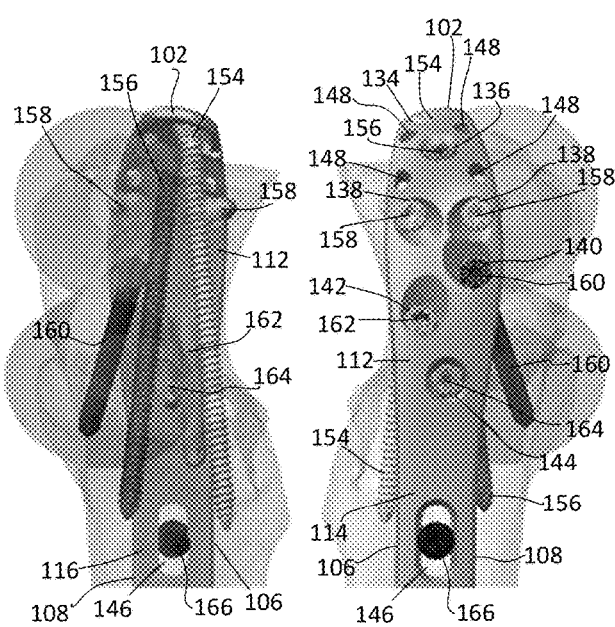
FIG. 4  FIG. 5  FIG. 6

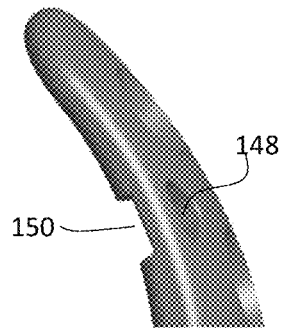
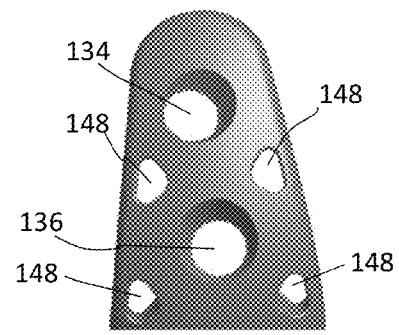
FIG. 14   FIG. 15
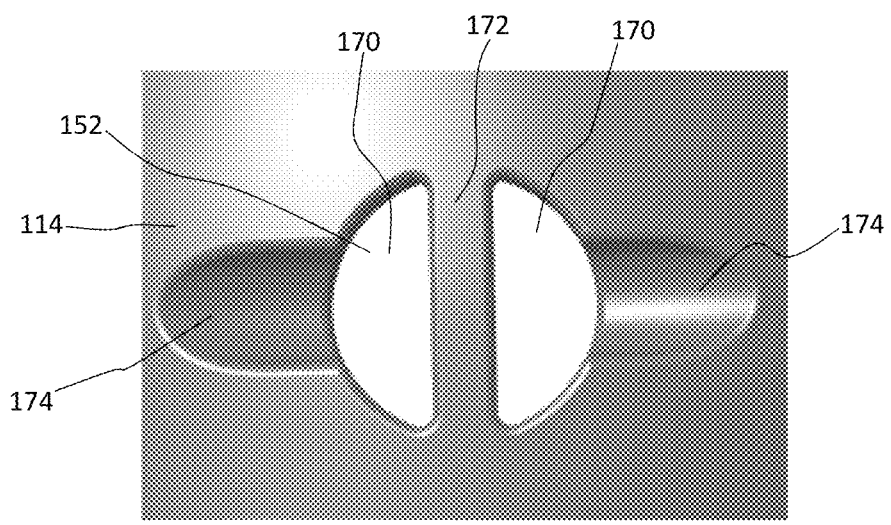
FIG. 16

BONE STABILIZATION SYSTEMS

FIELD OF THE INVENTION

The present disclosure relates to surgical devices, and more particularly, stabilization systems including plates, for example, for trauma applications.

BACKGROUND OF THE INVENTION

The ulna is a long bone found in the forearm that extends from the elbow to the smallest finger and is found on the medial side of the forearm. It runs parallel to the radius, the other long bone in the forearm, and is the larger and longer of the two bones. The proximal ulna consists of the olecranon process posteriorly and the coronoid process anteriorly. The olecranon process and the coronoid process define the greater sigmoid notch, which articulates with the trochlea of the humerus. The lesser sigmoid notch is located on the lateral aspect of the proximal ulna and articulates with the radial head. The olecranon acts as a posterior buttress, preventing anterior translation of the ulna, and is the site of triceps attachment. Bone fracture of the proximal ulna may be caused, for example, due to falls on the forearm or outstretched arm or direct impact from an object to the forearm.

Bone fractures can be healed using plating systems. During treatment, one or more screws are placed on either side of the fracture, thereby causing compression and healing of the fracture. There is a need for improved plating systems as well as designs to optimize screw trajectories and target critical anatomical areas.

SUMMARY OF THE INVENTION

In accordance with the application, in some embodiments, a system is provided for treating a fracture in a bone, such as a proximal ulna bone. The bone plate may have a head portion, a shaft portion, an upper surface and a lower surface configured to engage the bone. The head portion may include a first proximal-most opening, a plurality of second openings, and a third opening, with each of the openings extending from the upper surface to the lower surface. The third opening may have a protrusion on the upper surface of the plate around a first portion of the opening and a recess into the upper surface of the plate around a second portion of the opening. A first fastener is receivable within the first opening and configured to extend distally. A plurality of second fasteners are receivable within the plurality of second openings and configured to extend distally and/or laterally. A third fastener is receivable within the third opening and configured to extend in a direction reverse to the first and second fasteners. In particular, the third fastener may extend proximally towards the olecranon process of the ulna bone. The plurality of second fasteners may extend toward the coronoid process and/or the anterior cortex of the ulna.

In other embodiments, a system is provided for treating a fracture in a proximal ulna bone. The system includes a bone plate having a head portion, a shaft portion extending from the head portion, an upper surface and a lower surface configured to engage the bone. The head portion may include a first proximal-most opening generally oriented in a direction of a distal end of the ulna. The head portion may include a second plurality of openings targeted toward an anterior cortex of the ulna. The head portion may include a third plurality of openings targeted towards the anterior cortex of the ulna, and the third plurality of openings may be targeted differently than the second plurality of openings. The head portion may include a fourth plurality of openings targeted toward a coronoid process and/or laterally toward a lateral cortex of the ulna. The head portion may include a fifth opening targeted towards an olecranon process of the ulna bone. A first fastener is receivable within the first opening and configured to extend distally. A plurality of second fasteners are receivable within the plurality of second openings and configured to extend distally, anteriorly, and/or laterally. A plurality of third fasteners are receivable within the plurality of third openings and configured to extend distally, anteriorly, and/or laterally. A plurality of fourth fasteners are receivable within the plurality of fourth openings and configured to extend distally, anteriorly and/or laterally. A fifth fastener is receivable within the fifth opening and configured to extend in a direction reverse to all of the first, second, third, and fourth fasteners. The fifth opening may have a protrusion on the upper surface of the plate around a first portion of the opening and a recess into the upper surface of the plate around a second portion of the opening. The fifth fastener may extend proximally towards the olecranon process of the ulna bone.

In other embodiments, a bone plate is provided for treating a fracture in a proximal ulna bone. The bone plate includes a head portion, a shaft portion extending from the head portion, an upper surface and a lower surface configured to engage the bone. The head portion may include a first proximal-most opening generally oriented in a first direction of a distal end of the ulna. The head portion may include a second plurality of openings nominally targeted toward an anterior cortex of the ulna. The head portion may include a third plurality of openings targeted towards the anterior cortex, and the third plurality of openings may be targeted differently than the second plurality of openings. The head portion may include a fourth plurality of openings targeted toward a coronoid process and/or laterally toward a lateral cortex of the ulna. The head portion may include a fifth opening targeted towards the olecranon process of the ulna bone. The bone plate may be a universal plate where the shaft portion is straight in-plane or a handed plate where the shaft portion is curved with a left-handed or a right-handed curvature, thereby accommodating an ulnar bow.

In yet other embodiments, a method of securing a bone plate to an ulna bone includes positioning the bone plate against a proximal portion of the ulna bone, wherein the head portion is configured to contact the olecranon process and the shaft portion is configured to contact the shaft of the ulna bone. A fastener is secured through an elongate opening, thereby allowing for provisional placement of the plate and proximal-distal and/or medial-lateral adjustment of plate. After proper anatomical placement is achieved, additional fasteners may be secured through the head portion and/or the shaft portion of the plate. For example, a first plurality of fasteners may be positioned through polyaxial openings along the shaft; and a second plurality of fasteners may be positioned through openings in the head portion and targeted towards the distal end of the ulna, the coronoid process, the lateral cortex, the anterior cortex, and/or the olecranon process. In one embodiment, the plate is configured to target at least six proximal points of fixation with medial-lateral splay built in to resist the triceps and reduce pullout.

Also provided are kits including plates of varying shapes and sizes, fasteners including locking and non-locking screws, bone anchors, k-wires, insertion tools, sutures, suture buttons, and components for installing the same.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 4 is a side view of the proximal segment of an olecranon plate positioned against and secured to bone in accordance with one embodiment of the present application.

FIG. 5 is a bottom view of the proximal segment of the olecranon plate shown in FIG. 4.

FIG. 6 is a top view of the proximal segment of the olecranon plate shown in FIG. 4.

FIG. 14 is a close-up side perspective view of an olecranon plate with suture holes according to one embodiment.

FIG. 15 is a close-up top view of the plate with suture holes shown in FIG. 14.

FIG. 16 is a close-up top view of a plate with a central suture hole design in accordance with one embodiment.

DETAILED DESCRIPTION OF THE INVENTION

Embodiments of the present application are generally directed to devices, systems and methods for bone stabilization. Some embodiments are directed to bone plates that extend across bone members to treat one or more fractures. In one exemplary embodiment, one or more plates may be suitable for the fixation of fractures and fragments of the proximal ulna, for example.

Although plates are described herein for the treatment of the proximal ulna, it will be appreciated that the plates may be adapted to contact one or more of a radius, a femur, a distal tibia, a proximal tibia, a proximal humerus, a distal humerus, a clavicle, a fibula, bones of the foot, bones of the hand, or other suitable bone or bones. The bone plates may be curved, contoured, straight, or flat. The plates may have a head portion that is contoured to match a particular bone surface, such as an olecranon process. In addition, the plates may have a shaft portion that is contoured to match a bone surface, such as the shaft of the ulna. The plates may be adapted to secure small or large bone fragments, single or multiple bone fragments, or otherwise secure one or more fractures. In particular, the systems may include a series of trauma plates and screws designed for the fixation of fractures and fragments in the proximal portion of the ulna. Different bone plates may be used to treat various types and locations of fractures.

In some embodiments, one or more of the plates described herein can comprise olecranon plates. These plates can be used by a surgeon as an internal fixation device for a variety of fracture patterns of the proximal ulna. The one or more plates can provide a number of advantages, as will be discussed further below. In particular, the plates are designed to better accommodate anatomical features, such as the olecranon process, the ulnar bow, etc. Although fixation of the proximal ulna is exemplified herein, it will be appreciated by one skilled in the art that one or more features of the plates may be suitable in other anatomical locations.

Figure 1:
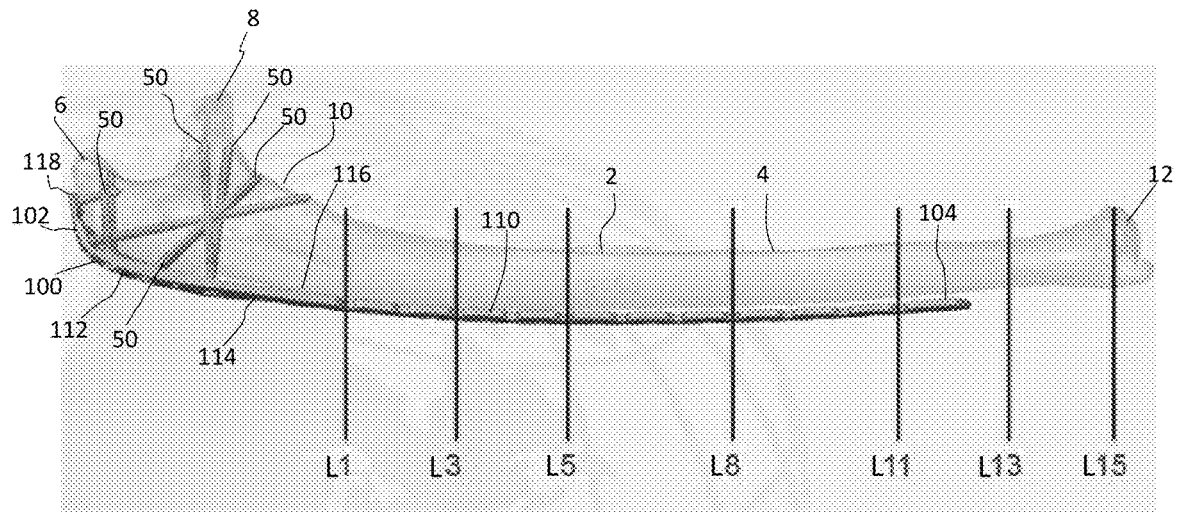
FIG. 1 is a view of a bone plate positioned against and secured to bone in accordance with some embodiments of the present application.

FIG. 1 shows a bone plate 100 affixed to bone in accordance with one embodiment of the present application. The bone plate 100 comprises an olecranon plate that is configured to be attached to a proximal portion of an ulna bone 2. The olecranon plate 100 comprises a proximal portion 102 and a distal portion 104. The proximal portion 102 comprises a head portion 112 that transitions into a shaft portion 110. The plate 100 includes an upper surface 114 and an opposed lower surface 116 configured to contact the bone 2. The shaft portion 110 of the bone plate 100 is configured such that the lower surface 116 resides along the shaft 4 of the ulna 2, and the lower surface 116 of the head portion 112 and/or proximal portion 102 of the bone plate 100 is configured to rest against the olecranon process 6 of the proximal end of the ulna 2. The olecranon process 6 forms the prominence of the elbow.

The plate 110 includes a first sidewall 106 and a second sidewall 108, opposite to the first sidewall 106, extending along its length between the proximal and distal portions 102, 104. Along the length of the bone plate 100 are one or more holes or openings 130, 134, 136, 138, 140, 142, 144, 146, 180 for receiving fasteners, screws, anchors, or the like therein. As shown in FIG. 1, the one or more plates 100 may be represented in a series of lengths. The lengths may be based on the number of holes or openings 130 provided in the shaft portion 110 of the plate 100 (namely, L1 is 1-hole, L3 is 3-holes, L5 is 5-holes, L8 is 8-holes, L11 is 11-hole, L13 is 13-holes, and L15 is 15-holes). Thus, different length plates 100 may be selected based on the anatomy of the patient, the type, location and number of fractures, or surgeon preference. Although these lengths including the specified number of holes 130 within the shaft portion 110 are exemplified, it is envisioned that other suitable numbers and configurations of holes or openings may be provided.

Figure 2:
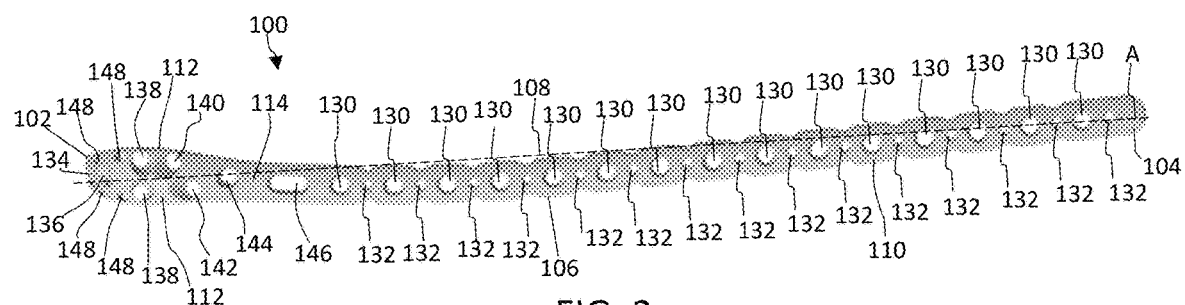
FIG. 2 is a top view of a left sided low-profile olecranon plate in accordance with one embodiment of the present application.

FIG. 2 depicts a low-profile plate 100 with an L15 length (e.g., having fifteen screw openings 130 along the shaft portion 110 of the plate 100). The low-profile plate 100 shown in FIG. 2 is left-sided and is configured to accommodate the anatomy of an ulnar bow. In other words, the plate 100 is curved along its length relative to a central longitudinal axis A extending between its proximal and distal ends 102, 104. With the left-sided curvature, the first side 106 is generally convex and the second side 108 is generally concave. It will be appreciated that a right-sided configuration (not shown) may also be available, which would be reversed, or a mirror image of the plate shown.

Figure 3:
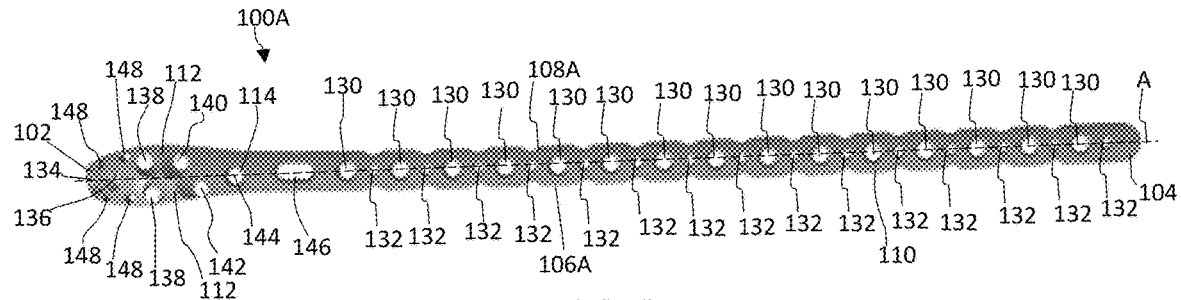
FIG. 3 is a top view of a universal olecranon plate in accordance with one embodiment of the present application.

In an alternative embodiment shown in FIG. 3, the low-profile plate 100A does not have specific left and right-sided designs. Instead, the low-profile plate 100A is a universal option, which has a straight shaft in-plane. In other words, the plate 100A extends along the central longitudinal axis A such that there is no curvature of the first and second sides 106A, 108A. Otherwise, the features of the plate 100A are the same or similar to the features of plate 100 and will be identified with the same reference numerals.

The bone plate 100, 100A includes one or more openings configured to receive one or more fasteners 50. The fasteners may include screws (e.g., screws 50A, 50B), anchors, pins, bolts, or other suitable means for fixation of the plate to bone. The fasteners may be locking, non-locking, threaded, partially threaded, curved, expandable, or otherwise configured to anchor the plate to bone. In some embodiments, one or more of the plates 100, 100A include locking and/or non-locking holes. Locking holes and locking fasteners may be useful for patients that have weaker bone. In addition, these may be helpful to prevent screw backout. Non-locking holes and fasteners may be useful for patients that have strong bone.

The bone plates described herein can include a combination of locking holes and non-locking holes, only locking holes, or only non-locking holes. Locking holes comprise one or more openings that accept one or more locking fasteners. The one or more openings can be partially or fully threaded, thread-forming, or otherwise configured to allow locking attachment of the fastener to the hole. In some embodiments, the holes comprise stacked or polyaxial locking holes, which can accept both locking and non-locking fasteners. In some embodiments, the locking fasteners include heads that are at least partially threaded. The locking fasteners can be monoaxial or polyaxial.

Non-locking holes comprise one or more openings for accepting one or more non-locking fasteners. The one or more openings are at least in part non-threaded. In some embodiments, these openings include non-threaded or stacked openings, which can accept both locking and non-locking fasteners. In some embodiments, the holes comprise stacked or polyaxial locking holes, which can accept both locking and non-locking fasteners. The non-locking fasteners can be monoaxial or polyaxial.

Figures 20, 21:
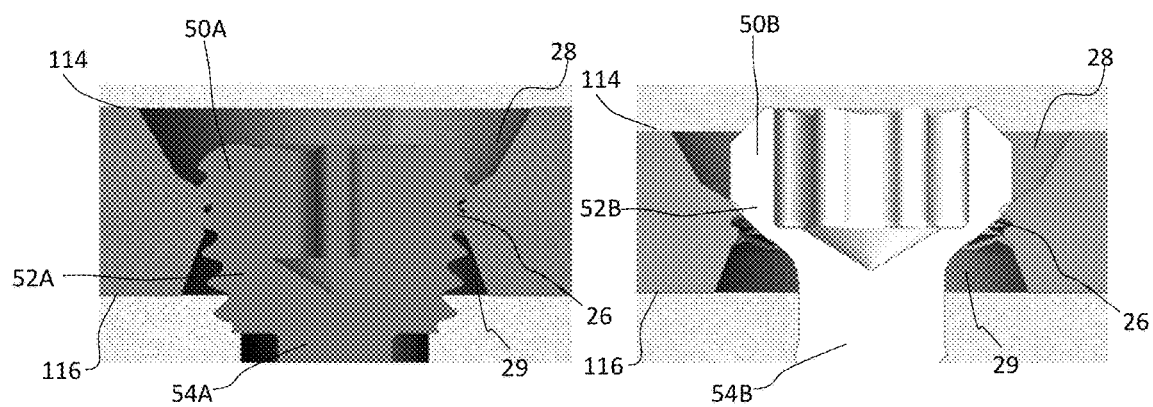
FIG. 20 is a close-up cross-sectional view of a polyaxial opening having a locking fastener therein.
FIG. 21 is a close-up cross-sectional view of the polyaxial opening shown in FIG. 20 having a non-locking fastener therein.

FIGS. 20 and 21 show examples of polyaxial screw hole geometry, which enables the use of locking fasteners 50A (FIG. 20) and non-locking fasteners 50B (FIG. 21). The fasteners 50A, 50B include a head portion 52A, 52B and a shaft portion 54A, 54B configured to engage bone, respectively. In FIG. 20, the locking mechanism is such that the screw head 52A has self-forming threads that work by displacement of the plate material. The screw 50A may be inserted within an angular cone of 40° inclusive where the force required to dislodge the head 52A of the screw at maximum angulation is sufficient to maintain angular stability, when compared to screws inserted perpendicular to the plate. Any of the holes or openings in the plate 100, 100A may be shaped such that the fastener 50A, 50B may be inserted at different angles. The geometry of the opening is conducive to catching the threads on the head portion 52A of the fastener 50A and to reduce the axial force necessary to initiate the thread formation. In FIG. 21, the head portion 52B is non-locking and does not include any threads.

An upper portion of the hole may be tapered 28, for example, with a conical straight tapered surface cut through the top surface 114 of the plate 100 for clearance of the head portion 52A, 52B of the fastener 50A, 50B during off angle insertion. A lower portion of hole may further be tapered 29, for example, with a conical straight tapered surface cut through the bottom surface 116 of the plate 100, 100A for clearance of the shaft portion 54A, 54B during off angle insertion. The upper tapered portion 28 may be larger, for example, with a larger degree of taper than the lower tapered portion 29. The upper and/or lowered tapered portions 28, 29 may be substantially conical or may be segmented with more than one section, such as two separate conical sections having different diameters or degrees of taper.

At the intersection between the upper tapered portion 28 and the lower tapered portion 29 a narrowed central portion may have a textured portion 26. As described herein, the textured portion 26 may include threads, ridges, bumps, dimples, serrations, or other types of textured areas. The texture portion 26 may provide a positive surface for the self-forming threads to cut into, thereby helping to lock the newly formed threads into the plate 100, 100A. More detailed examples of locking and non-locking fasteners and openings are shown and described in U.S. Publication No. 2018/0049782, which is hereby incorporated by reference in its entirety for all purposes.

Figure 22:
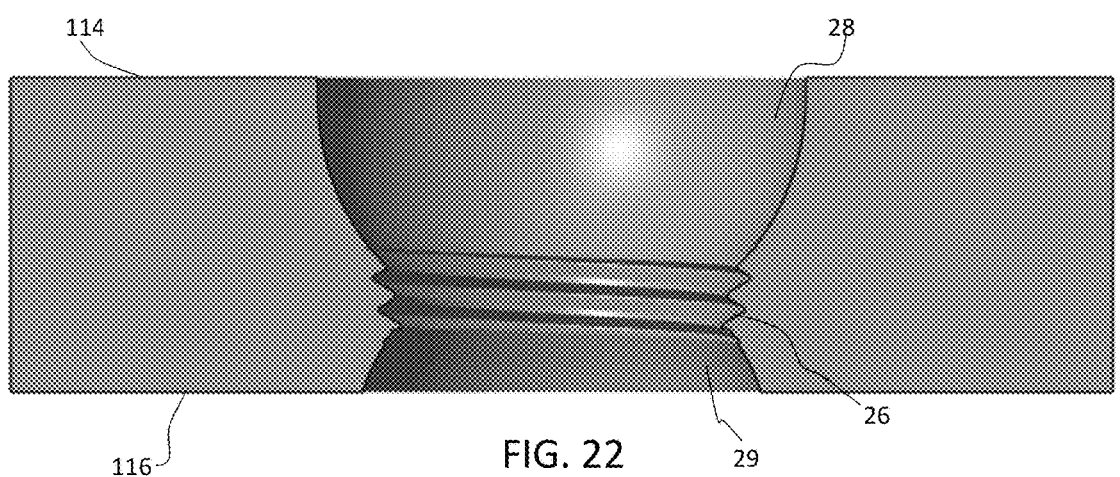
FIG. 22 is a close-up cross-sectional view of an undercut stacked hole geometry, which may be included in one or more embodiments of the plate.

FIG. 22 depicts another embodiment of hole geometry that may be suitable for use with one or more embodiments of the olecranon plate 100, 100A. FIG. 22 depicts an undercut stacked hole geometry with a threaded portion 26 capable of accepting locking screws, a spherical recess 28 at the top surface 114 capable of accepting non-locking screws 50A, and an undercut 29 at the bottom surface 116 which is capable of accepting collet mechanism drill guides. More detailed examples of suitable openings are shown and described in U.S. Publication No. 2018/0049782, which is hereby incorporated by reference in its entirety for all purposes.

Turning now to the plate embodiment shown in FIG. 2, the left-sided plate 100 includes a plurality of polyaxial holes 130, 134, 136, 138, 140, 142, 144 both proximally and distally. These polyaxial holes 130, 134, 136, 138, 140, 142, 144 may have a 2.5 mm screw option, thereby enabling a thinner plate profile. For the 2.5 mm design, the thickness of the plate 100 may be held at 2 mm along the shaft 110, tapering to a thickness of less than 2.75 mm along the proximal olecranon tip to enable closing of the fascia. In the universal plate 100A shown in FIG. 3, the polyaxial holes 130, 134, 136, 138, 140, 142, 144 may have a 2.5 mm screw option, but may also feature 3.5 mm polyaxial, monoaxial, stacked or undercut stacked holes. In some embodiments, the universal plate 100A includes both 2.5 mm and 3.5 mm polyaxial openings 130, 134, 136, 138, 140, 142, 144. For the 2.5/3.5 mm universal design, the thickness of the plate 100A may be held at 3 mm along the shaft 110, tapering to a thickness of less than 2.75 mm along the proximal olecranon tip.

The plates 100, 100A may include one or more k-wire holes 132 for receiving a k-wire therein. One or more k-wires may guide the bone plate 100 to a desired surgical site. The k-wire holes 132 allow for temporary fixation of the bone plate 100, 100A to bone via the k-wire. In some embodiments, one or more of the k-wire holes 132 is unthreaded. As shown in FIGS. 2 and 3, the k-wire holes 132 may be alternatingly positioned between respective polyaxial holes 130 along the shaft portion 110 of the plate 100. In other words, a k-wire hole 132 may be positioned between every polyaxial hole 130 along the shaft 110 of the plate 100, 100A.

Turning now to FIGS. 4-6, the head portion 112 of the plate 100 may include one or more openings 134, 136, 138, 140, 142, 144 to aim one or more fasteners 50 along optimized screw trajectories. The trajectories of the proximal portion 102 of the plate 100 may be aligned so that their nominal axes allow for fixation in critical anatomical areas for the average proximal ulna 2.

By way of example, the head portion 112 may include one or more of the following openings 134, 136, 138, 140, 142, 144 in order to optimize fixation of the proximal ulna 2. As noted herein, the openings 134, 136, 138, 140, 142, 144 may include, for example, locking holes, non-locking holes, polyaxial holes, monoaxial holes, stacked holes, undercut stacked holes, or any combination thereof.

A first opening 134 may be provided at the proximal-most tip of the plate 100. The first opening 134 may be configured to receive a first fastener 154. The first fastener may be generally oriented such that the distal end of the fastener 154 is inserted nominally towards the distal end 12 of the ulna 2. The first fastener 154 may be positioned generally parallel to the shaft portion 110 of the plate 110. The first fastener 154 may be oriented distally, anteriorly, and/or laterally. In a preferred embodiment, the first fastener 154 is oriented distally, anteriorly, and laterally.

A second opening 136 may be provided through plate 100 such that a second fastener 156 inserted therein is nominally angled toward the anterior cortex 10 of the bone. The second opening 136 may be positioned distal to the first opening 134. The second fastener 156 may be oriented distally, anteriorly, and/or laterally. In a preferred embodiment, the second fastener 156 is oriented distally, anteriorly, and laterally. The second fastener 156 may extend laterally outward towards side 108 while first fastener 154 may extend laterally outward towards side 106.

Third and fourth openings 138 may be provided in the head portion 112 such that one or more fasteners 158 are generally positioned towards the olecranon process 6 and targeted nominally laterally outward. The fasteners 158 may be oriented anteriorly and/or laterally. In a preferred embodiment, the fasteners 158 are oriented anteriorly and laterally in diverging directions. The third fastener 158 may extend laterally outward towards side 108 while fourth fastener 158 may extend laterally outward towards side 106.

The fifth opening 140 may be provided adjacent to one of openings 138 such that fastener 160 inserted in opening 140 is generally targeted toward the coronoid process 8 and laterally toward the lateral cortex of the bone. The fastener 160 may be oriented distally, anteriorly, and/or laterally. In a preferred embodiment, the fastener 160 is oriented distally, anteriorly, and laterally.

The sixth opening 142 is configured to receive fastener 162, which may be angled toward the anterior cortex 10. The fastener 162 may be oriented distally, anteriorly, and/or laterally. In a preferred embodiment, the fastener 162 is oriented distally and anteriorly.

The seventh opening 144 is configured to receive fastener 164, which is directed towards the coronoid process 8 and may be positioned generally perpendicular to the plate 100. The fastener 164 may be oriented anteriorly and/or laterally. In a preferred embodiment, the fastener 164 is oriented only anteriorly.

The lengths of fasteners 154, 156, 158, 160, 162, 164 may be selected to target the desired anatomical areas. For example, fasteners 154, 156 may have greater lengths than fasteners 160, 164, and fasteners 158 may be shorter than fastener 162. Although certain lengths may be preferred, it will be appreciated that lengths may be selected based on patient anatomy, fracture type or location, surgeon preference, or the like.

The trajectories exemplified herein may provide for up to a total of six proximal points of fixation with medial-lateral splay built in to resist the triceps and reduce pullout. Additionally, the nominal construct enables the use of two cross-fracture screws both aimed toward a cortex and several options for rafting. Although these openings 134, 136, 138, 140, 142, 144 and fasteners 154, 156, 158, 160, 162, 164 are exemplified, it will be appreciated that other configurations may be suitable to target the proximal olecranon tip, coronoid, anterior cortex, and/or lateral cortex of the ulna 2.

Figures 7, 8:
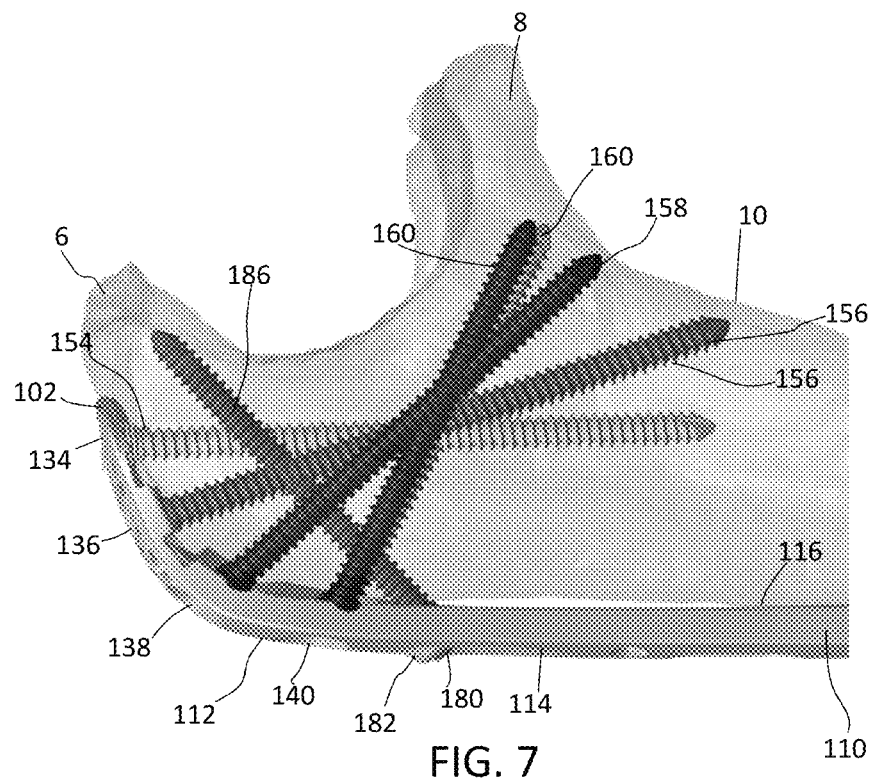
FIG. 7 is a side perspective view of the proximal segment of another embodiment of an olecranon plate with the bone fasteners having overlapping trajectories.
FIG. 8 is a close-up top view of overlapping hole identifiers for the proximal plate segment according to one embodiment.

According to another embodiment, the construct may incorporate one or more overlapping screw trajectories. Proximal fixation in the olecranon 6 may be important for reducing comminuted fragments and preventing construct pullout due to triceps forces. For this reason, a surgeon may desire to have as many points of fixation proximally as possible. Overlapping screw trajectories may help to address this issue. With emphasis on FIG. 7, the overlapping trajectories may allow for more screw options to be included in the plate design, thereby giving surgeons the flexibility to pick and choose which fasteners or screws to use based on the fracture pattern and anatomy. A screw or fastener may only overlap with one or two other screws or fasteners and all overlapping holes may be denoted with one or markings 176. The marking or markings 176 may include an easily identifiable laser mark, for example, as shown in FIG. 8. The marking 176 may include a ring or partial ring around the opening 138, 140. The marking 176 may include two or more concentric rings or partial rings around one or more of the openings 138, 140.

The trajectories shown in FIG. 7 may include first opening 134, at the proximal-most tip of the head portion 112, with fastener 154 generally oriented in the direction of the distal end 12 of the ulna 2. One or more openings 136, positioning one or more fasteners 156, may be nominally targeted toward the anterior cortex 10 of the bone. One or more openings 138 with one or more fasteners 158 may be oriented towards anterior cortex 10. One or more openings 140, positioning one or more fasteners 160, may be generally targeted toward the coronoid process 8 and/or laterally toward the lateral cortex of the bone. Opening 180 with fastener 186 may be a reverse angle screw generally oriented backwards toward the olecranon process 6. In other words, fastener 186 may be positioned in a direction opposite to all of the other fasteners 154, 158, 160 in the plate 100. Fastener 154 may be positioned substantially perpendicular to the shaft portion 110 of the plate 100. Fasteners 158, 160 may be provided at an acute angle relative to the shaft portion 110 of the plate 100, and fastener 186 may be provided at an obtuse angle relative to the shaft portion 110 of the plate 100. Thus, the fasteners 154, 156, 158, 160, 186 are aimed toward different proximal targets.

Figure 9:
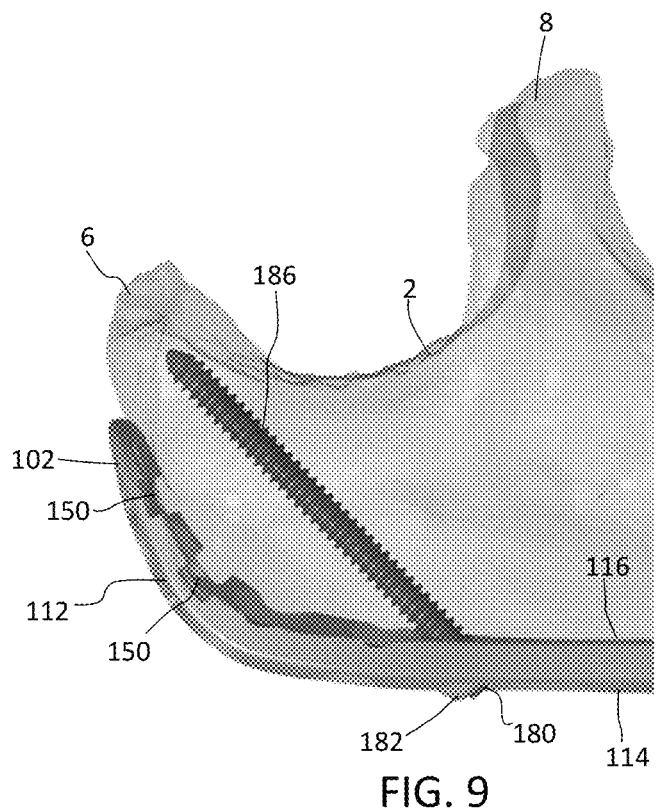
FIG. 9 is a side perspective view of a plate with a reverse angle fastener according to one embodiment.
Figure 10:
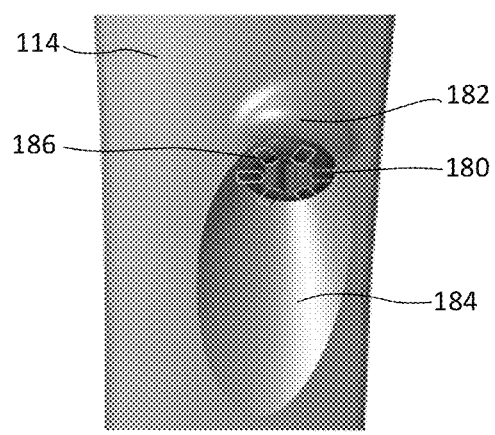
FIG. 10 is a close-up view of the head of a reverse angle fastener and an eyebrow or protrusion on the top surface of the plate according to one embodiment.

With further emphasis on FIGS. 9 and 10, the reverse angle fastener 186 may provide improved fixation at the proximal olecranon 6. The triceps is a powerful force acting on the olecranon 6 and one of the leading causes of construct pullout. To counteract this force, it may be desirable to have as many screws of fasteners crossing the fracture line as possible. Fasteners positioned in the proximal-distal direction may be considered a "home run" screw.

Another option that may be included in some embodiments of the olecranon plate 100 is a reverse angle home run screw 186. The reverse angle fastener 186 runs distal-proximal (as best seen in FIG. 7) crossing the fracture line, but in the opposite direction to all of the other fasteners in the construct. Due to its severe reverse angle, the opening 180 may include an eyebrow or protrusion 182, which may be a rounded thickness of material on the top surface 114 of the plate 100 that opposes the angle of the hole 180. The protrusion 182 may help to prevent screw thread prominence without requiring the entire plate to be thicker at that location. As best seen in FIG. 10, the opening 180 includes protrusion 182 on the upper surface 114 of the plate 100 around a first portion of the opening 180 (e.g., toward the proximal end) and a recess 184 defined into the upper surface 114 of the plate 100 around a second portion of the opening 180 (e.g., toward the distal end). The eyebrow or protrusion 182 may include a bump, ridge, or convex protrusion extending upward from the upper surface 114 of the plate 100. The protrusion 182 may be rounded, curved, angled, or otherwise configured. The protrusion 182 increases the thickness of the plate 100 at the location of the protrusion 182 and the remainder of the plate 100 maintains its low-profile thickness. Opposite to the protrusion 182 is the recess 184 cut into the upper surface 114 of the plate 100. The recess 184 may include an arcuate cutout, chamfer, or other depression. The recess 184 decreases the thickness of the plate 100 at the location of the recess 184 and the remainder of the plate 100 maintains its low-profile thickness. The recess 184 allows for insertion of the fastener 186 at the extreme angle necessary to target the olecranon process 6 of the ulna 2.

Figure 11:
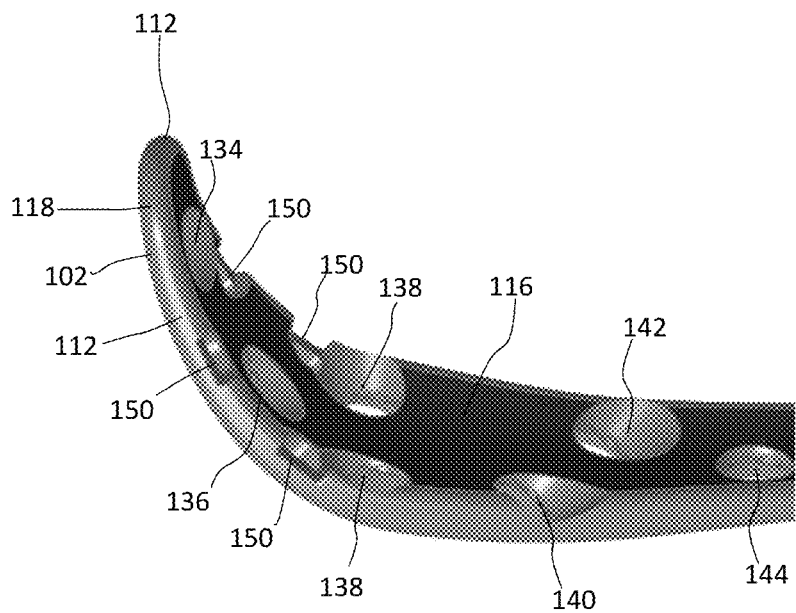
FIG. 11 is a side perspective view of the proximal segment of the olecranon plate according to one embodiment.

Turning now to FIG. 11, the plate 100 or a portion thereof may have an optimized plate contour. In particular, the anatomic contour along the bottom surface 116 of the plate 100 may be configured to follow the best approximation of average proximal ulna anatomy. The bottom surface 116 may be concavely curved along its length and/or its width. The plate 100 may further include a proximal impingement chamfer 118. The chamfer 118 or taper on the proximal tip of the plate 100 may help to insure minimal bony and soft-tissue impingement of the olecranon fossa and triceps.

Figure 19:
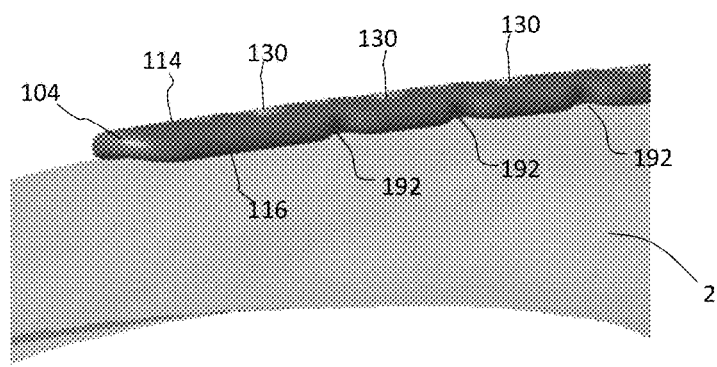
FIG. 19 is a close-up perspective view of a distal segment of one embodiment of the olecranon plate having a concave bottom surface.

Also, with emphasis on FIG. 19, the distal portion 104 of the plate 100 may include a concavity to contour to the anatomy of the shaft 4 of the bone 2. When initially placing olecranon plates 100, the distal end 104 may kick off the bone, which may require the surgeon to reposition the plate. To reduce the likelihood of this, the shaft 110 of the plate 100 may be contoured to have a sizeable concavity that will hug the ulnar ridge and increase the resistance of kickoff.

Figures 12, 13:
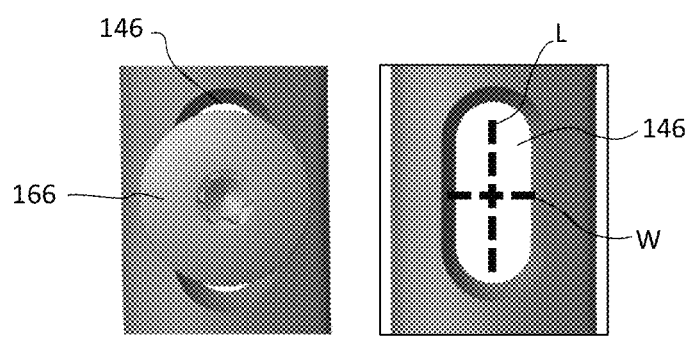
FIG. 12 is a close-up top view of a fastener positioned in a two-axis positioning slot according to one embodiment.
FIG. 13 is a close-up top view of the two-axis positioning slot shown in FIG. 12.

Turning now to FIGS. 12 and 13, the plate 100, 100A may include a two-axis positioning slot 146. The slot 146 may allow for proximal-distal (P-D) adjustment and/or medial-lateral (M-L) adjustment of plate during provisional placement. The slot 146 may have a length L greater than its width W. The width W may be generally greater than an outer diameter of the shaft of a fastener 50. The length L allows for the proximal-distal adjustment of the plate 100, and the width W allows for the medial-lateral adjustment of the plate 100. The two-axis positioning slot 146 may allow surgeons to optimally center the plate position along the shaft 4 of the bone 2 prior to installing any locking screws. Additionally, the slot 146 may be etched with laser lines, for example, spaced 1 mm from each other, for more accurate adjustment. While the present embodiment illustrates a single slot 146, in some embodiments, there could be additional positioning slots.

In some embodiments, the plate construct may be reinforced with augmenting sutures through the tendon, thereby increasing the ultimate load to failure following olecranon plate fixation. To accommodate this need, one or more types of suture holes 148, 152 can be incorporated into any of the plates described herein. Turning to FIGS. 14 and 15, the plate 100 may include one or more suture holes 148, which are intended for insertion of the suture along the sides of the plate 100, 100A. The suture holes 148 may be generally triangular in shape with squared or rounded undercuts 150 to ease suture needle insertion. The sharp edges may be heavily broken to prevent tearing of the suture. With reference to FIG. 16, a second suture hole design 152 is intended for insertion of the suture from the top surface 114 of the plate 100 in order to avoid blockage of the needle by the bone. The suture hole 152 may be generally circular in shape with two types of undercuts to ease needle insertion: a circular swept cut 174 that mimics the shape of the needle and a standard circular cut from the back surface of the plate that lifts the center tab 172 off the bone. The suture hole 152 may be divided into two sections 170 by the tab 172, thereby forming two half circle sections 170 on either side of the tab 172. The swept cuts 174 may be positioned on either side of the sections 170 and may extend generally perpendicular to the orientation of the tab 172.

Figure 17:
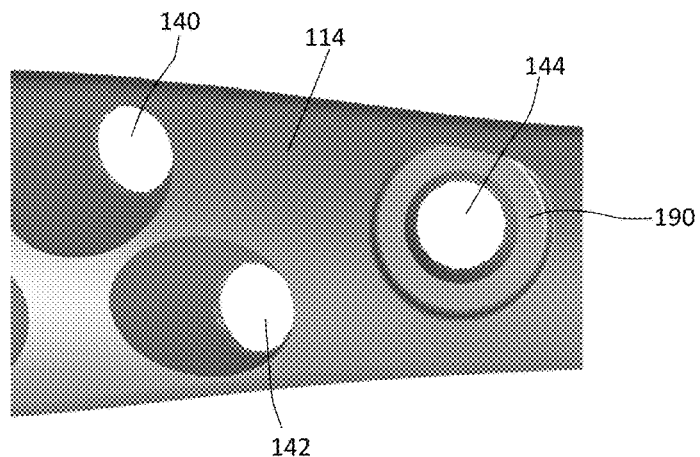
FIG. 17 is a close-up top view of a suture button recess according to one embodiment.

Turning now to FIG. 17, one or more of the openings may be modified for receipt of a suture button (not shown). Fractures of the coronoid are difficult to treat and, when coupled with olecranon fracture dislocation or terrible triad injuries, often require additional fixation outside of plating. To enable the fixation of the coronoid using suture in conjunction with an olecranon plate 100, a suture button recess 190 at the coronoid screw hole (e.g., opening 144) can be included in one or more embodiments of the plate. The suture button recess 190 may include a recess or indentation into the upper surface 114 of the plate 100 and surrounding the opening 144. The recess or inset 190 into the top surface 114 of the plate 100 allows for a suture button (not shown) to be firmly secured to the plate 100, thereby minimizing translational movement of the button when secured to the bone. More detailed examples of suture buttons and openings are shown and described in U.S. Publication No. 2018/0049782, which is hereby incorporated by reference in its entirety for all purposes.

Figure 18:
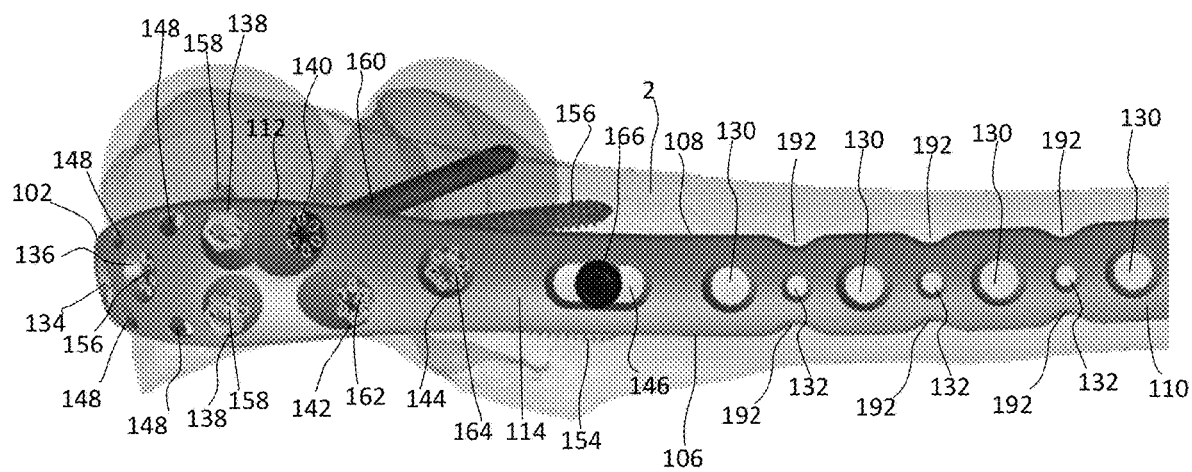
FIG. 18 is a top perspective view of one embodiment of the olecranon plate having a plurality of scallops along one or more sides of the plate.

Turning to FIG. 18, the edges 106, 108 of the shaft portion 110 of the plate 100 may include one or more waisted edge scallops 192. Variances in ulnar anatomy often result in surgeons in-plane bending the shaft 110 of olecranon plates during surgery. In order to make bending easier and reduce the likelihood of deformation at the shaft holes 130, one or more scallops 192 can be added between shaft holes 130. In particular, the indentations of the scallops 192 can align with each of the k-wire holes 132 provided along the shaft 110 of the plate 100. With the scallops 192 acting as a bend location guide, the surgeon can utilize plate bending irons in the system to contour the plate to best fit the anatomy of the patient.

The bone plates may be comprised of titanium, stainless steel, cobalt chrome, carbon composite, plastic or polymer—such as polyetheretherketone (PEEK), polyethylene, ultra-high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Similarly, the bone plates may receive one or more screws or fasteners may be comprised of titanium, cobalt chrome, cobalt-chrome-molybdenum, stainless steel, tungsten carbide, combinations or alloys of such materials or other appropriate biocompatible materials. In one embodiment, the plate is constructed of a softer material (e.g., implant grade Ti, Ti alloys, and/or SS alloy) than the screw (e.g., cobalt chromium alloy, Kolsterized SS alloy, Dotized type II anodized Ti) to facilitate displacement of plate material during the thread-forming process. Although the above list of materials includes many typical materials out of which bone plates and fasteners are made, it should be understood that bone plates, fasteners, or other components may be comprised of any appropriate materials.

One skilled in the art will appreciate that the embodiments discussed above are non-limiting. While bone plates may be described as suitable for a particular location (e.g., proximal ulna) or approach, one skilled in the art will appreciate that the bone plates can be used for multiple locations and approaches. In addition, while bone plates are described as having particular holes (e.g., locking or non-locking), one skilled in the art will appreciate that any of the bone plates can include locking, non-locking or a combination of locking and non-locking holes. In addition to the bone plates, fasteners, and instruments described above, one skilled in the art will appreciate that these described features can be used with a number of trauma treatment instruments and implants, including external fixators, ring fixators, rods, and other plates and screws. It will also be appreciated that one or more features of one embodiment may be partially or fully incorporated into one or more other embodiments described herein.

What is claimed is:

1. A system for treating a fracture in a proximal ulna bone, the system comprising:
   a bone plate having a head portion being curved and shaped to wrap around an olecranon, a shaft portion extending from the head portion, an upper surface, and a lower surface configured to engage the bone, the head portion having a first proximal-most opening, a plurality of second openings positioned distally of the first opening, and a third opening positioned distally of the second openings, each extending from the upper surface to the lower surface, the third opening having a protrusion rising above the upper surface of the plate around a first portion of the opening and a recess into the upper surface of the plate around a second portion of the opening;
   a first fastener receivable within the first opening and configured to extend distally toward a distal end of an ulna;
   a plurality of second fasteners receivable within the plurality of second openings and configured to extend distally, anteriorly, and/or laterally;
   a third fastener receivable within the third opening and configured to extend in a direction reverse to all of the first and second fasteners;
   a positioning fastener, the positioning fastener having a head portion; and
   a two-axis positioning slot disposed on the shaft portion and distally of the head portion, the two-axis positioning slot sized to allow the positioning fastener to adjust the bone plate in a proximal-distal direction and medial-lateral direction,
   wherein a diameter of the head portion of the positioning fastener is larger than the width of the two-axis positioning slot, and
   wherein the shaft portion includes a plurality of shaft holes and a k-wire hole disposed between each of the plurality of shaft holes,
   wherein the head portion includes a side wall extending downwardly from the upper surface and a suture hole disposed distally of the first opening and proximally of the second openings, the side wall including an associated undercut to ease insertion of a suture needle, the undercut also being disposed distally of the first opening and proximally of the second openings.

2. The system of claim 1, wherein the third fastener is adapted to extend toward an olecranon process of the ulna.

3. The system of claim 1, wherein the plurality of second fasteners are adapted to extend toward a coronoid process of the ulna.

4. The system of claim 1, wherein the plurality of second fasteners are adapted to extend toward an anterior cortex of the ulna.

5. The system of claim 1, wherein the lower surface of the plate includes a curvature at the head portion such that the upper surface is convex and the lower surface is concave.

6. The system of claim 5, wherein the lower surface of the head portion is contoured to approximate a proximal ulna anatomy.

7. The system of claim 1, wherein the plate is a universal plate and the shaft portion is straight in-plane.

8. The system of claim 1, wherein the plate is a handed plate and the shaft portion is curved with a left-handed or a right-handed curvature.

9. The system of claim 1, wherein the side wall of the shaft portion comprises first and second sidewalls defining waisted edge scallops.

10. The system of claim 9, wherein the waisted edge scallops of the first side wall defines a first indentation and the waisted edge scallops of the second sidewall defines a second indentation, and wherein the first and second indentations are aligned with one of the k-wire holes.

11. The bone plate of claim 1, wherein waisted edge scallops are disposed between each of the plurality of shaft holes and are aligned with each of the k-wire holes.

12. A system for treating a fracture in a proximal ulna bone, the system comprising:
   a bone plate having a head portion being curved and shaped to wrap around an olecranon, a shaft portion extending from the head portion, an upper surface and a lower surface configured to engage the bone, the head portion having a first proximal-most opening oriented to be in a direction of a distal end of the ulna, a second plurality of openings positioned distally of the first opening and configured to be in a direction of an anterior cortex of the ulna, a third plurality of openings positioned distally of the second openings and configured to be in a direction of the anterior cortex of the ulna, the third plurality of openings being oriented to be targeted differently than the second plurality of openings, a fourth plurality of openings configured to be in a direction of a coronoid process and/or laterally toward a lateral cortex of the ulna, and a fifth opening configured to be in a direction of an olecranon process of the ulna bone;

a first fastener receivable within the first opening and configured to extend distally toward a distal end of an ulna;

a plurality of second fasteners receivable within the plurality of second openings and configured to extend distally, anteriorly, and/or laterally;

a plurality of third fasteners receivable within the plurality of third openings and configured to extend distally, anteriorly, and/or laterally;

a plurality of fourth fasteners receivable within the plurality of fourth openings and configured to extend distally, anteriorly and/or laterally; and a fifth fastener receivable within the fifth opening and configured to extend in a direction proximally and reverse to all of the first, second, third, and fourth fasteners;

a positioning fastener, the positioning fastener having a head portion; and a two-axis positioning slot disposed on the shaft portion and distally of the head portion, the two-axis positioning slot sized to allow the positioning fastener to adjust the bone plate in a proximal-distal direction and medial-lateral direction, wherein a diameter of the head portion of the positioning fastener is larger than the width of the two-axis positioning slot, and wherein the shaft portion includes a plurality of shaft holes and a k-wire hole disposed between each of the plurality of shaft holes, wherein the head portion includes a side wall extending downwardly from the upper surface and a suture hole disposed distally of the first opening and proximally of the second openings, the side wall including an associated undercut to ease insertion of a suture needle, the undercut also being disposed distally of the first opening and proximally of the second openings.

13. The system of claim 12, wherein the fifth opening has a protrusion on the upper surface of the plate around a first portion of the opening and a recess into the upper surface of the plate around a second portion of the opening.

14. The system of claim 12, wherein the fifth fastener is configured to extend proximally towards an olecranon process of the ulna bone.

15. A bone plate for treating a fracture in a proximal ulna bone, the bone plate comprising:

a head portion, a shaft portion extending from the head portion, an upper surface and a lower surface configured to engage the bone, the head portion having a first proximal-most opening configured to be oriented in a first direction of a distal end of the ulna, a second plurality of openings positioned distally of the first opening and configured to be targeted toward an anterior cortex of the ulna, a third plurality of openings positioned distally of the second openings and configured to be targeted towards the anterior cortex of the ulna, the third plurality of openings being targeted differently than the second plurality of openings, a fourth plurality of openings configured to be targeted toward a coronoid process and/or laterally toward a lateral cortex of the ulna, and a fifth opening configured to be targeted towards an olecranon process of the ulna bone;

a positioning fastener, the positioning fastener having a head portion; and a two-axis positioning slot disposed on the shaft portion and distally of the head portion, the two-axis positioning slot sized to allow the positioning fastener to adjust the bone plate in a proximal-distal direction and medial-lateral direction, wherein a diameter of the head portion of the positioning fastener is larger than the width of the two-axis positioning slot, and wherein the shaft portion includes a plurality of shaft holes and a k-wire hole disposed between each of the plurality of shaft holes, wherein the head portion includes a side wall extending downwardly from the upper surface and a suture hole disposed distally of the first opening and proximally of the second openings, the side wall including an associated undercut to ease insertion of a suture needle, the undercut also being disposed distally of the first opening and proximally of the second openings.

16. The bone plate of claim 15, wherein the lower surface of the plate includes a curvature at the head portion such that the upper surface is convex and the lower surface is concave, and wherein the lower surface of the head portion is contoured to approximate a proximal ulna anatomy.

17. The bone plate of claim 15, wherein the plate is a universal plate and the shaft portion is straight in-plane.

18. The bone plate of claim 15, wherein the plate is a handed plate and the shaft portion is curved with a left-handed or a right-handed curvature.

19. The bone plate of claim 15, wherein the side wall of the shaft portion comprises first and second sidewalls defining waisted edge scallops, wherein the waisted edge scallops of the first side wall defines a first indentation and the waisted edge scallops of the second sidewall defines a second indentation, and wherein the first and second indentations are aligned with one of the k-wire holes.

* * * * *